US008105772B2

(12) United States Patent
Inouye et al.

(10) Patent No.: US 8,105,772 B2
(45) Date of Patent: Jan. 31, 2012

(54) DNA DETECTION METHOD USING MOLECULAR BEACON WITH THE USE OF MONOMER EMISSION/EXCIMER EMISSION SWITCHING OF FLUORESCENT MOLECULE

(75) Inventors: Masahiko Inouye, Toyama (JP);
Kazuhisa Fujimoto, Toyama (JP);
Hisao Shimizu, Toyama (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 1029 days.

(21) Appl. No.: 10/571,133

(22) PCT Filed: Aug. 18, 2004

(86) PCT No.: PCT/JP2004/011819
§ 371 (c)(1),
(2), (4) Date: Aug. 27, 2008

(87) PCT Pub. No.: WO2005/026390
PCT Pub. Date: Mar. 24, 2005

(65) Prior Publication Data
US 2009/0018320 A1 Jan. 15, 2009

(30) Foreign Application Priority Data
Sep. 11, 2003 (JP) .................................. 2003-320311

(51) Int. Cl.
*C12Q 1/68* (2006.01)
*C07H 21/02* (2006.01)
*C07H 21/04* (2006.01)
(52) U.S. Cl. ........................ 435/6.1; 536/23.1; 536/24.3
(58) Field of Classification Search ...... 435/6; 536/23.1, 536/24.3
See application file for complete search history.

(56) References Cited

U.S. PATENT DOCUMENTS
5,925,517 A * 7/1999 Tyagi et al. ........................ 435/6

FOREIGN PATENT DOCUMENTS
JP 2003-510017 A 3/2003
WO WO00/79009 * 12/2000
WO WO 03/052134 A2 6/2003

OTHER PUBLICATIONS

Michel et al. [Tetrahedron 58 : 7975-7982 (2002)].*
Balakin et al. Biosensors & Bioelectronics 13 : 771-778 (1998).*
Ebata et al. Photochemistry and Photobiology 62 (5) : 836-839 (1995).*
Tyagi et al. Nature Biotechnology 18 : 1191-1196 (2000).*
Ebata et al. Nucleic Acid hybridization accompanied with excimer formation from two pyrene-labeled probes. Photochemistry and Photobiology 62 (5) : 836-839 (1995).*
Paris et al .Probing DNA sequences in solution with a monomer-excimer fluorescence color change. Nucleic Acids Research 26(16) : 3789-3793 (1998).*
Michel et al., Tetrahedron, Elsevier Science Publishers, vol. 58, No. 39, pp. 7975-7982, 2002, XP004381453.
Sanjay Tyagi et al.; Nature Biotechnology, vol. 14, pp. 303-308, Mar. 1996.
Sanjay Tyagi et al.; Nature Biotechnology, vol. 18, pp. 1191-1196, Nov. 2000.
Weihong Tan et al.; Chem. Eur. J., 6, No. 7, pp. 1107-1111, 2000.
Peng Zhang et al.; Angew. Chem. Int. Ed. 2001, 40, No. 2, pp. 402-405.
Balakin K.V. et al., Biosensors & Bioelectronics, 1998, vol. 13, pp. 771 to 778.
Henegariu O. et al., Nat Biotechnol. 2000, vol. 18, No. 3, pp. 345 to 348.
Yamana K. et al., Nucleic Acids Symposium Series, 1992, vol. 27, pp. 135 to 136.
Fujimoto K. et al., J. Org. Chem., May 2004, vol. 69, pp. 3271 to 3275.
A. Yamane, "MagiProbe: a novel fluorescence quenching-based oligonucleotide probe carrying a fluorophore and an intercalator," Nucleic Acids Research, Oct. 1, 2002, vol. 30, No. 19, pp. 1-8.
EPO extended European Search Report, Appl. No. 09002776.4, May 10, 2010, pp. 1-8.

* cited by examiner

*Primary Examiner* — Ethan Whisenant
(74) *Attorney, Agent, or Firm* — Birch, Stewart, Kolasch & Birch, LLP

(57) ABSTRACT

It is intended to provide a means and a method whereby a molecule for DNA detection at an elevated accuracy can be provided, different form the existing DNA detection system with the use of a molecular beacon. A molecular beacon wherein fluorescent organic groups capable of forming an excimer are bonded to the 3' and 5' ends of a single-stranded oligonucleotide to be hybridizable with a subject oligonucleotide and the switching of monomer emission/excimer emission is utilized; and a method of detecting SNP by using this molecular beacon.

18 Claims, 3 Drawing Sheets

F: Fluorescent organic group capable of forming excimer
X: Base of a nucleic acid
n,m = 2~8 e.g., pyrene

Example of the molecular beacon according to the present invention

Example of synthesis scheme of a fluorescent organic group that can modify both 3' and 5' ends using the same starting compound (a) LiAlH$_4$, THF, (b) ($^i$Pr$_2$N)$_2$PO(CH$_2$)$_2$CN, 1H-tetrazole, acetonitrile,
(c) KOH, methanol, (d) N,N'-disuccinimidyl carbonate, acetonitrile, pyridine Equivalent of the subject nucleotide added to
the molecular beacon according to the present invention

DNA DETECTION METHOD USING MOLECULAR BEACON WITH THE USE OF MONOMER EMISSION/EXCIMER EMISSION SWITCHING OF FLUORESCENT MOLECULE

FIELD OF THE INVENTION

The present invention is related to a molecular beacon that may be used for a method of detecting a complementary strand DNA sequence and a method of detecting SNP.

BACKGROUND OF THE INVENTION

The conventional molecular beacons contain a fluorescent organic group and a quenching organic group that are covalently bonded to each of the ends of a single-stranded oligonucleotide having a hair-pin loop structure. When an oligonucleotide having a subject sequence that can form a double strand with the loop region is absent, the fluorescent organic group and the quenching organic group will be located in the vicinity to each other due to a stem structure formed by the sequence of the both ends of the beacons so as to cause Fluorescence Resonance Transfer (FRET). As a result, the emission by the fluorescent organic group will be quenched by the quenching organic group. On the other hand, when the oligonucleotide having the subject sequence coexist with the molecular beacons, such sequence will form a double strand with the loop region of the molecular beacons so that the fluorescent organic group and the quenching organic group will be located in such a distance that FRET cannot occur. As a result, the emission by the fluorescent organic group will be revived. The beacons may be also used in the detection of SNP wherein a subject oligonucleotide having a complementary sequence except a single base cannot revive the emission by the fluorescent organic group.

The conventional DNA probe molecule based on excimer emission (complex between ground-state and excited state molecules of the same kind of a fluorescent organic molecule, which has emission with a longer wavelength than that of the monomer emission) uses two kinds of proves wherein the proves are covalently bonded to a fluorescent organic group capable of forming the excimer, and form a three-dimensional complex with an oligonucleotide having the subject complementary sequence.

Non-Patent Document 1: Tyagi, S.; Kramer, F. R. Nat. Biotechnol. 1996, 14, 303-308
Non-Patent Document 2: Tyagi, S.; Marras, S. A. E.; Kramer, F. R. Nat. Biotechnol. 2000, 18, 1191-1196
Non-Patent Document 3: Tan, W.; Fang, X.; Li, J.; Liu, X. Chem. Eur. J. 2000, 6, 1107-1111
Non-Patent Document 4: Zhang, P.; Beck, T.; Tan, W.; Angew. Chem., Int. Ed. 2001, 40, 402-405

SUMMARY OF THE INVENTION

The conventional molecular beacons have a disadvantage that they cannot detect an unexpected event such as quenching due to other quenching molecules than the quenching organic group or departure of the fluorescent organic group. The excimer emission DNA probe molecule utilizing formation of the three-dimensional complex also has a problem that it has a larger loss in entropy and a weaker complex-forming ability than the two-dimensional probe molecules.

The present inventor has studied to provide a DNA detective molecule with an elevated accuracy by adopting a detection system different from the conventional molecular beacons.

As a result, the present invention was accomplished based on the development of a molecular beacon wherein a fluorescent organic group capable of forming an excimer is covalently bonded to both the 5' and 3' ends of a single-stranded oligonucleotide to be hybridized with a subject oligonucleotide, and the switching of monomer emission and excimer emission is utilized.

Thus, a first aspect of the present invention is related to a molecular beacon wherein the both ends of a single-stranded oligonucleotide having a hair-pin loop structure are modified with the same kind of fluorescent organic groups, especially those capable of forming an excimer.

A second aspect of the present invention relates to a method for the synthesis of the molecular beacon.

And a third aspect of the present invention relates to a method of detecting a complementary stand DNA or SNP wherein a subject oligonucleotide sequence is detected with the use of switching from excimer emission to monomer emission of a fluorescent organic group.

The molecular beacon according to the present invention enables the detection of the subject oligonucleotide sequence with a very elevated accuracy and sensitivity. The switching from excimer emission to monomer emission will not occur when the subject oligonucleotide comprises one base that is not complementary. The present invention may be therefore utilized in the detection of SNP as well.

BEST MODE FOR CARRYING OUT THE INVENTION

Figure 1:
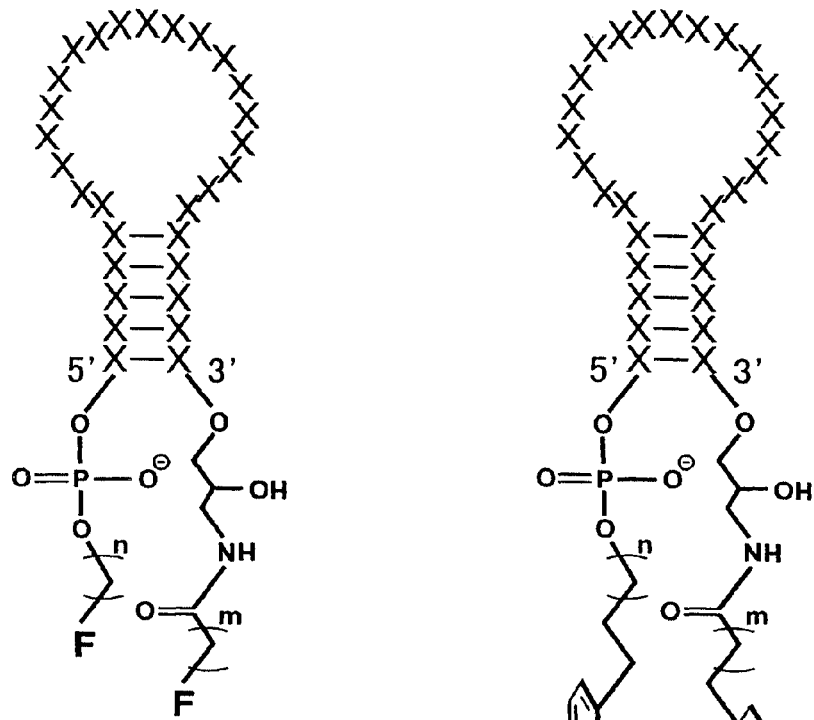
FIG. 1 shows a structure of the molecular beacon (SEQ ID NO: 1) according to the present invention.
Figure 1:
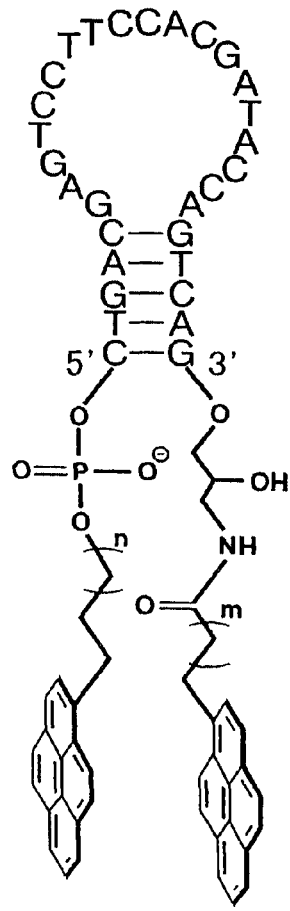

The molecular beacon according to the present invention is a DNA probe molecule that can detect a mismatched base pair with a high selectivity. Its structure is characterized by that the both ends of a single-stranded oligonucleotide having a hair-pin loop structure are modified by the same kind of fluorescent organic groups. There is no restriction for such fluorescent organic groups as long as they are capable of forming an excimer. A structure of the molecular beacon according to the present invention is shown in FIG. 1.

The fluorescent organic groups that may be used in the present molecular beacon include pyrene or its derivatives, and naphthalenes, fluorines and cyanine pigments.

Although there is no limit in the number of bases that constitute the single-stranded oligonucleotide of the present molecular beacon, the single-stranded oligonucleotide shall have usually 24-34 bases, preferably 26-32 bases in view of detection sensitivity. Furthermore, the hair-pin loop structure, which will hybridize with the complementary oligonucleotide in the subject DNA molecule, usually consists of 15-22 bases, preferably of 17-20 bases.

It is preferred that the fluorescent organic group in the present molecular beacon is bonded to both 5' and 3' ends of the single-stranded oligonucleotide via a spacer with an appropriate length and structure, so that the two fluorescent organic groups will occupy such a spatial position that they can be associated by a hydrophobic interaction when the subject oligonucleotide sequence hybridizable with the present molecular beacon is not present.

There is no limit in the structure and length of the spacer as long as the above conditions are met. For example, at least one of the spacer may contain a methylene group having 2-8 carbon atoms. Other constituents such as oxygen, nitrogen and sulfur atoms can be contained in the spacer.

The molecular beacon according to the present invention may be synthesized by means of any method known for those skilled in the art by optionally selecting appropriate starting and intermediate materials and reaction conditions depending on the kinds of the fluorescent organic groups and the like.

For example, a phosphoroamidite derivative of the fluorescent organic group may be used as a derivative for modification of the 5' end, and a succinimidyl derivative of the fluorescent organic group may be used as a derivative for modification of the 3 end. Those derivatives may be synthesized from a methyl ester of the fluorescent organic group. More specifically, the phosphoroamidite and succinimidyl derivatives are synthesized with the use of a methyl ester of 3-pyrenylpropionic acid, or the fluorescent organic group may be bonded to the 3' end by reacting its succinimidyl derivative with an amino group at the 3' end.

A method of detecting a complementary stand DNA or SNP according to the present invention is characterized by detecting a subject oligonucleotide sequence or SNP comprised therein with the use of switching from excimer emission to monomer emission of the fluorescent organic group.

More specifically, the switching from excimer emission to monomer emission of the fluorescent organic group in the molecular beacon of the present invention will occur when the subject oligonucleotide sequence hybridizes with the oligonucleotide sequence in the hair-pin region of the molecular beacon so as to break a complex formed through association with hydrophobic interaction. The complementary stand DNA (oligonucleotide sequence) or SNP therein, i.e., complementarity between the above oligonucleotides may be detected by detecting the above switching.

The length of the subject oligonucleotide sequence that is detectable by the present detecting method almost corresponds to that of the base sequence in the hair-pin region of the present molecular beacon, being usually 15-22 bases, preferably 17-20 bases.

The present invention will be explained more in detail below, which shall not limit the scope of the present invention in any way.

Example 1

Figure 2:
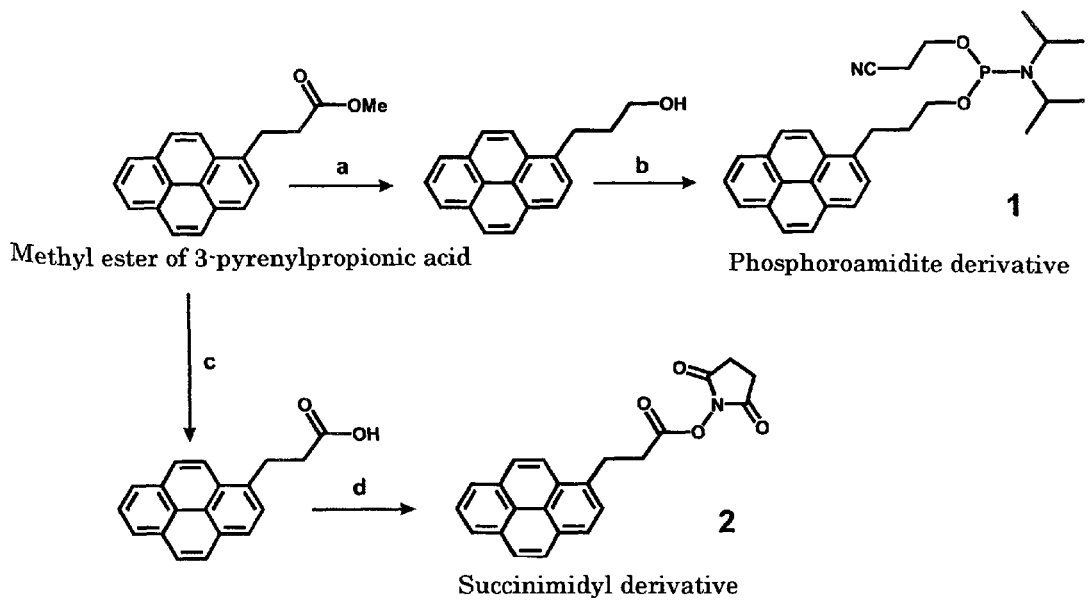
FIG. 2 shows an example of the synthesis of the derivative of the fluorescent organic group that is used in a method of the synthesis according to the present invention.

Two kinds of pyrene derivatives were synthesized so that a fluorescent organic group, pyrene, capable of forming an excimer can be covalently bonded to the 5' and 3' ends of a single-stranded oligonucleotide having 29 bases. As illustrated in FIG. 2, a phosphoroamidite derivative (1) was synthesized as a derivative for modification of the 5' end, and a succinimidyl derivative (2) was synthesized as a derivative for modification of the 3' end with the use of a methyl ester of 3-pyrenylpropionic acid.

Thus, to a $CH_3CN$ (3 ml) solution of 1H-tetrazole (80.7 mg, 1.15 mmol) and 2-cyanoethyl tetraisopropylphosphorodiamidite (463 mg, 1.54 mmol) was added a $CH_3CN$ solution (12 ml) of 3-(1-pyrenyl)propanol (200 mg, 0.77 mmol) dropwise at 0° C. After the solution had been stirred at a room temperature for 2 h, the solvent was removed by a rotary evaporator. The residue was poured into $NaHCO_3$ aqueous solution and extracted with ethyl acetate. The ethyl acetate extract was evaporated by a rotary evaporator and chromatographed (silica gel pre-treated with hexane:$Et_3N$=50:1; eluent, hexane:$CH_2Cl_2$=6:1) to give phosphoroamidite derivative (1) (oil): yield 68% (242 mg). The physicochemical properties of the phosphoroamidite derivative (1) are as follows:

IR (KBr) 3041, 2966, 2872, 2251, 1462, 1369, 1183, 1127, 1028, 977, 942, 845 $cm^{-1}$; $^1$H NMR ($CDCl_3$, 500 MHz) δ 1.21 (dd, J=6.5, $J_{P-H}$=1.5 Hz, 12H), 2.17 (m, 2H), 2.63 (t, J=7 Hz, 2H), 3.44 (t, J=8 Hz, 2H), 3.62-3.91 (m, 8H), 7.88 (d, J=8 Hz, 1 H), 7.96-8.03 (m, 3H), 8.08-8.16 (m, 4H), 8.29 (d, J=9 Hz, 1H);

$^{13}$C NMR ($CDCl_3$, 125 MHz) δ 20.35, 20.40, 24.57, 24.62, 24.67, 29.86, 33.15, 33.21, 42.98, 43.08, 58.15, 58.30, 63.06, 63.20, 117.67, 123.36, 124.67, 124.78, 124.82, 124.95, 125.04, 125.77, 126.57, 127.21, 127.32, 127.47, 128.63, 129.81, 130.85, 131.37, 136.13;

high-resolution ESI-MS m/e calcd for $C_{28}H_{33}N_2O_2P$ (M+Na$^+$) 483.2177, found 483.2197.

Then, a $CH_3CN$ (30 ml) solution of 3-(1-pyrenyl)propionic acid (340 mg, 1.24 mmol), pyridine (105 μl), and 1N,N-disuccinimidyl carbonate (333 mg, 1.30 mmol) was stirred at 50° C. for 2.5 h. After removal of the solvent by a rotary evaporator, the residue was dissolved in saturated NaCl aqueous solution and extracted with ethyl acetate. The ethyl acetate extract was evaporated by a rotary evaporator and chromatographed (silica gel; eluent, $CH_2Cl_2$) to give succinimidyl derivative (2): yield 82% (378 mg). The physicochemical properties of the succinimidyl derivative (2) are as follows:

mp 179-181° C.;

IR (KBr) 3043, 2946, 1782, 1737, 1596, 1370, 1214, 1070, 848 $cm^{-1}$;

$^1$H NMR ($CDCl_3$, 500 MHz) δ 2.87 (br s, 4H), 3.16 (t, J=8 Hz, 2H), 3.80 (t, J=8 Hz, 2H), 7.93 (d, J=7.5 Hz, 1H), 8.00-8.05 (m, 3H), 8.13-8.21 (m, 4H), 8.25 (d, J=9 Hz, 1H);

$^{13}$C NMR ($CDCl_3$, 125 MHz) δ 25.60, 28.23, 32.70, 122.53, 124.87, 125.03, 125.07, 125.08, 125.23, 127.04, 127.10, 127.43, 128.00, 128.50, 130.48, 130.76, 131.33, 132.87, 167.95, 169.10;

high-resolution ESI-MS m/e calcd for $C_{23}H_{17}NO_4$ (M$^+$) 371.1158, found 371.1123.

The modification of the 5% end of the single-stranded oligonucleotide (DNA) having 29 bases by the fluorescent organic group was done by reaction with the phosphoroamidite derivative (1) using an automatic DNA synthesizer according to a usual manner. The resulting single-stranded DNA molecule with 29 bases having the modified 5' end was purified by means of HPLC with the use of COSMOSIL 5$C_{18}$-MS-II column (4.6×150 mm; Nakalai Tesque). The DNA molecule was eluted with an eluent of 0.05M ammonium formate and a linear gradient of acetonitrile (0-20%) at a rate of 1.0 mL/min.

DMSO solution (14 μl) containing the succinimidyl derivative (2) (250 μg) was added into a 0.1M sodium bicarbonate solution (86 μl, pH8.5) containing the above single-stranded DNA molecule with 29 bases having the modified 5' end (100 μg). The reaction solution was kept for 12 hours at a room temperature, while being washed several times with $CHCl_3$. The resulting aqueous phase was purified by means of HPLC under the same conditions as described above except for a linear gradient of acetonitrile (5-85%) to give a molecular beacon according to the present invention (the compound (3) in FIG. 1). The resulting molecular beacon was confirmed and identified with an absorption wavelength derived from pyrene (λ det: 340 nm) and an absorption wavelength derived from a nucleic acid (λ det: 254 nm)

Example 2

$T_m$ of the molecular beacon containing the synthesized fluorescent organic groups that were covalently bonded thereto was determined according to a usual manner. Thus, electronic absorption spectra were recorded on a V-560 UV/VIS spectrophotometer (JASCO) in a temperature range of from 10 to 90° C. controlled by an ETC-505T Temp. Controller (JASCO) by using a solution containing the molecular beacon (2 μM), 5 mM $MgCl_2$, 50 mM KCl, and 20 mM Tris-HCl (pH 8.0). The $T_m$ value was calculated by a Spectra Manager for Windows DNA Melting Program (JASCO).

As a result, $T_m$ of the molecular beacon prepared in Example 1 was 59° C., while that of a non-modified oligonucleotide (29-mer) having no pyrene bonded to the ends was 46° C. These results suggested that the two fluorescent organic groups (pyrenes) associated with each other by a hydrophobic interaction functioned as an extra base pair so as to contribute to stabilization of a double strand.

Figure 3:
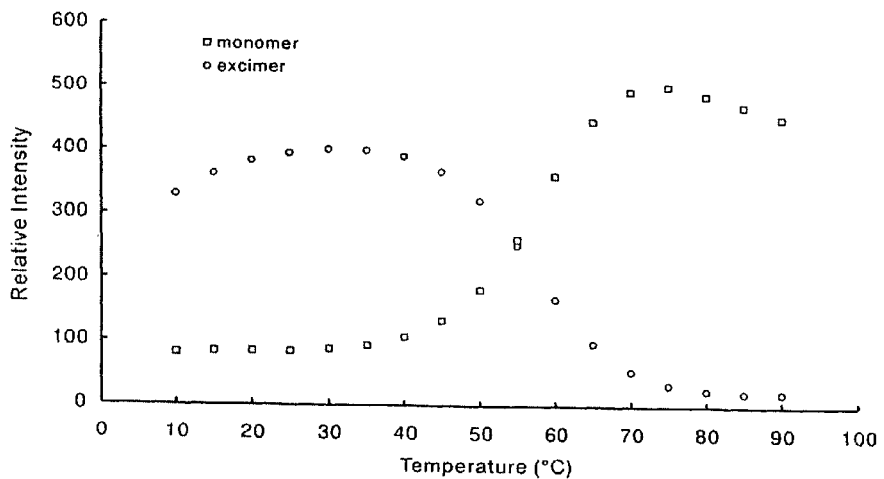
FIG. 3 shows the switching of monomer emission and excimer emission in accordance with the change of temperature.

It was further confirmed that while an excimer emission prevailed in the above molecular beacon solution at a temperature under $T_m$, the excimer emission would gradually decrease and transfer to an monomer emission at a temperature above $T_m$. In other words, it was confirmed that the switching from excimer emission to monomer emission of the fluorescent organic group (pyrene) was accomplished with the use of the oligonucleotide having the hair-pin loop structure. Fluorescence spectra were recorded on a FP-6500 fluorophotometer (JASCO) in a temperature range of from 10 to 90° C. controlled by an ETC-505T Temp. Controller (JASCO) with an excitation wavelength of 345 nm and emission wavelength of 382 nm (monomer) and 498 nm (excimer). These results are shown in FIG. 3.

Example 3

A complementary strand was detected under the following conditions with the use of the same devices as in Example 2. To a 200 nM solution of the molecular beacon synthesized in Example 1 containing 5 mM $MgCl_2$, 50 mM KCl, and 20 mM Tris-HCl (pH 8.0) was added an oligonucleotide consisting of 19 bases complementary to the loop region of the above molecular beacon (0.1 equiv×10) at 25° C. Each mixture was stirred at 25° C. until no more change of the fluorescence spectra occurred (about 15 min). The excitation wavelength was 345 nm, and the fluorescence spectra were recorded from 300 to 650 nm. The excimer emission disappeared and switched to the monomer emission at a stage when almost an equal amount of the oligonucleotide had been added. Since intensity of the monomer emission was not be increased any more by a further addition of the same oligonucleotide beyond the equal amount, the molecular beacon according to the present invention was confirmed to be a very selective DNA probe molecule.

Figure 4:
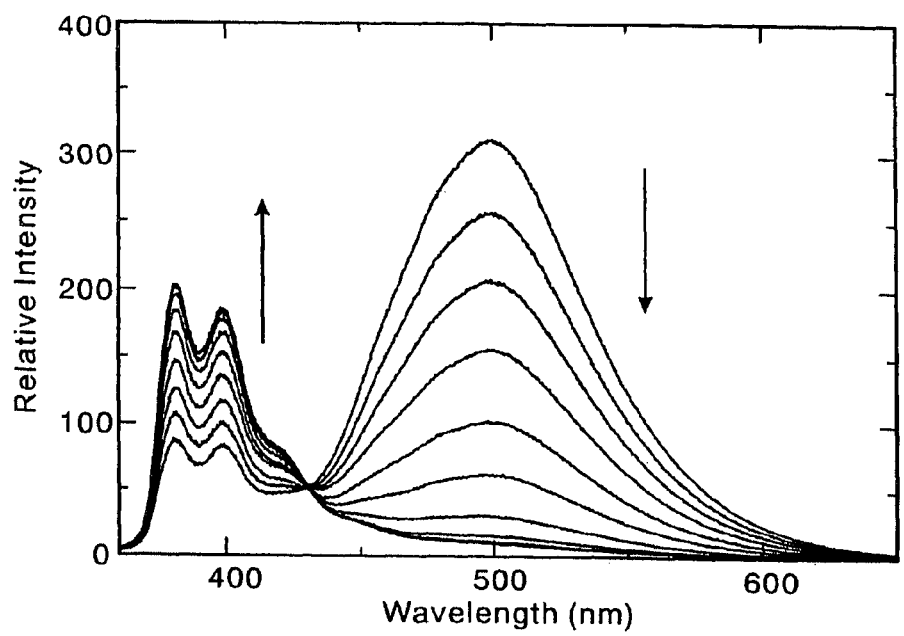
FIG. 4 shows the results of the detection of the complementary stand DNA with the use of the molecular beacon of the present invention.

It was observed that a ratio of (monomer emission intensity $(I_{382nm})$)/(excimer emission intensity $(I_{498nm})$) was 0.2 in the absence of the complementary oligonucleotide, but it became 20 at the detection thereof, showing change of about 100 times. It was also found that detection limit with respect to the concentration was ≦1 nM (containing 20% DMF), showing that the molecular beacon according to the present invention is comparable or superior to the conventional molecular beacons. These results are shown in FIG. 4.

Example 4

Figure 5:
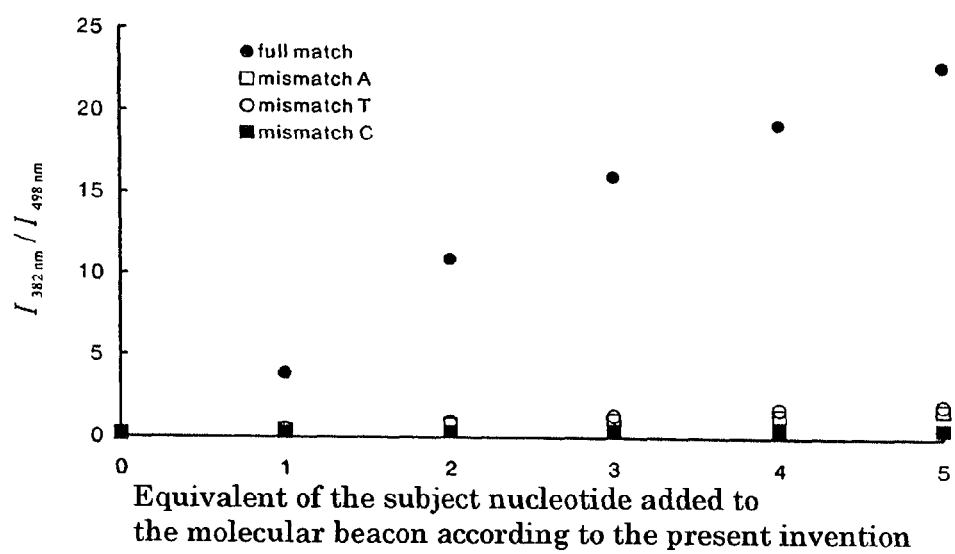
FIG. 5 shows the results of the detection of the SNP with the use of the molecular beacon of the present invention.

A mismatch in base pairs (SNP) was detected under the following conditions with the use of the same devices as in Example 2. To a 5 nM solution (the buffer used in Example 3 with 20% DMF) was added each of such a completely complementary oligonucleotide and three oligonucleotides comprising one mismatched base (SNP) as shown in Table 1 (1 equiv×5) at 25° C. While the switching from excimer emission to monomer emission was observed at the addition of the completely complementary oligonucleotide, the intensity of fluorescence hardly changed at the addition of the three oligonucleotides comprising SNP. These results are shown in FIG. 5.

TABLE 1

Molecular beacon according to the
present invention (e.g., pyrene):

5'-(1-pyrenyl)-$CH_2)_3$-<u>CTGAC</u>GAGTCCTTCCACGATA
CCA<u>GTCAG</u>-($C_3NHCOC_2H_4$)-(1-pyrenyl)-3' (SEQ ID NO: 1)

Oligonucleotide sequence of
the above molecular beacon:

5'-<u>CTGAC</u>GAGTCCTTCCACGATACCA<u>GTCAG</u>-3'
(SEQ ID NO: 1)

Sequence complementary to the loop region
of the above molecular beacon:

5'-TGGTATCGTGGAAGGACTC-3' (SEQ ID NO: 2)

Sequence complementary to the loop region of
the above molecular beacon except for one base:

5'-TGGTATCGT<u>A</u>GAAGGACTC-3' (SEQ ID NO: 3)

5'-TGGTATCGT<u>T</u>GAAGGACTC-3' (SEQ ID NO: 4)

5'-TGGTATCGT<u>C</u>GAAGGACTC-3' (SEQ ID NO: 5)

The above results have a very important meaning. An appearance probability of a DNA chain having 19 base pairs in the genome will be only once throughout a sequence of $4^{19}=2.7\times10^{11}$ bases, which is much longer than $2.4\times10^{11}$ bases of a liliaceae that has the largest genome size in all of the organisms of the earth. This means that the molecular beacon according to the present invention has such a selectivity that it can detect only one particular base sequence among all of the organisms.

INDUSTRIAL APPLICABILITY

By utilizing the switching from excimer emission to monomer emission according to the present invention, simplification of the synthesis of the molecular beacon was succeeded. The molecular beacon is a very sensitive DNA probe that is responsive to almost an equal mount of a subject oligonucleotide sequence, and it can detect a mismatched base pair at a low concentration with a high selectivity.

What is claimed:

1. A method of detecting a complementary strand DNA comprising:
determining whether fluorescent organic groups, which modify both ends of a first oligonucleotide, switch from excimer emission to monomer emission upon hybridization of the first oligonucleotide and a subject oligonucleotide,
wherein detection of the switch to monomer emission indicates that the subject oligonucleotide is complementary to the first oligonucleotide.

2. A method of detecting a complementary strand DNA comprising:
hybridizing a hair-pin loop region of a single stranded oligonucleotide of a molecular beacon and a subject oligonucleotide sequence, wherein both ends of the single stranded oligonucleotide are modified with the same kind of fluorescent organic groups, and
determining whether the fluorescent organic groups of the molecular beacon switch from excimer emission to monomer emission,
wherein detection of the switch to monomer emission indicates that the subject oligonucleotide is complementary to the hair-pin loop region of the single stranded oligonucleotide of the molecular beacon.

3. The method of detecting a complementary strand DNA of claim 1 wherein the subject oligonucleotide sequence consists of 15-22 bases.

4. The method of detecting a complementary strand DNA of claim 3 wherein the subject oligonucleotide sequence consists of 17-20 bases.

5. A method of detecting a SNP in a subject oligonucleotide comprising:
determining whether fluorescent groups, which modify both ends of a first oligonucleotide switch from excimer emission to monomer emission upon hybridization of the first oligonucleotide and a subject oligonucleotide,
wherein failure to detect the switch to monomer emission indicates that the subject oligonucleotide sequence comprises a SNP.

6. A method of detecting a SNP in a subject oligonucleotide sequence comprising:
hybridizing a hair-pin loop region of a single stranded oligonucleotide of a molecular beacon and a subject oligonucleotide sequence, wherein both ends of the single stranded oligonucleotide are modified with the same kind of fluorescent organic groups, and
determining whether the fluorescent organic groups of the molecular beacon switch from excimer emission to monomer emission,
wherein failure to detect the switch to monomer emission indicates that the subject oligonucleotide sequence comprises a SNP.

7. The method of detecting the SNP of claim 5 wherein the subject oligonucleotide sequence consists of 15-22 bases.

8. The method of detecting the SNP of claim 7 wherein the subject oligonucleotide sequence consists of 17-20 bases.

9. A method of detecting a complementary strand DNA or a subject oligonucleotide comprising a SNP
hybridizing a hair-pin loop region of a single stranded oligonucleotide of a molecular beacon and a subject oligonucleotide sequence, wherein said subject oligonucleotide optionally comprises a SNP, and wherein both ends of the single stranded oligonucleotide are modified with the same kind of fluorescent organic groups, and
determining whether the fluorescent organic groups of the molecular beacon switch from excimer emission to monomer emission,
wherein failure to detect the switch to monomer emission indicates that the subject oligonucleotide comprises a SNP and wherein detection of the switch to monomer emission indicates that the subject oligonucleotide is complementary to the oligonucleotide in the hair-pin loop region.

10. The method of claim 9 wherein the fluorescent organic group is a residue of pyrene or its derivative.

11. The method of claim 9 wherein the single-stranded oligonucleotide has 24-34 bases.

12. The method of claim 11 wherein the single-stranded oligonucleotide has 26-32 bases.

13. The method of claim 9 wherein the hair-pin loop region consists of 15-22 bases.

14. The method of claim 13 wherein the hair-pin loop region consists of 17-20 bases.

15. The method of claim 9 wherein the fluorescent organic group is bonded to both 5' and 3' ends of the single-stranded oligonucleotide via a spacer with an appropriate length.

16. The method of claim 15 wherein at least one of the spacers contains a $(CH_2)_{2-8}$ group.

17. The method of claim 9, wherein the subject oligonucleotide sequence consists of 15-22 bases.

18. The method of claim 17, wherein the subject oligonucleotide sequence consists of 17-20 bases.

* * * * *

SEQUENCE LISTING

<160> NUMBER OF SEQ ID NOS: 5

<210> SEQ ID NO 1
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 1
ctgacgagtc cttccacgat accagtcag                29

<210> SEQ ID NO 2
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 2
tggtatcgtg gaaggactc                19

<210> SEQ ID NO 3
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 3
tggtatcgta gaaggactc                19

<210> SEQ ID NO 4
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 4
tggtatcgtt gaaggactc                19

<210> SEQ ID NO 5
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 5
tggtatcgtc gaaggactc                19